US00PP28108P2

(12) United States Plant Patent
Van Dijk

(10) Patent No.: US PP28,108 P2
(45) Date of Patent: Jun. 13, 2017

(54) ***ANTHURIUM* PLANT NAMED 'ANTHDUDKA'**

(50) Latin Name: ***Anthurium andreanum* L.**
Varietal Denomination: ANTHDUDKA

(71) Applicant: ANTHURA B. V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/999,294

(22) Filed: Apr. 21, 2016

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

PLUTO Plant Variety Database Mar. 17, 2017. p. 1.*

* cited by examiner

*Primary Examiner* — Annette Para

(74) *Attorney, Agent, or Firm* — Jondle & Associates, P.C.

(57) ABSTRACT

A new and distinct *Anthurium* plant named 'ANTHDUDKA' particularly distinguished by having shiny, bright red, cordate and very durable spathes that retain the original color for a very long period of time, dark green and long cordate, durable leaves, white spadix with yellow tip, early and rich flowering continuously throughout the year and a plant height of 26.0 cm to 28.0 cm, is disclosed.

3 Drawing Sheets

Genus and species: *Anthurium andreanum* L.
Variety denomination: 'ANTHDUDKA'.

BACKGROUND OF THE NEW PLANT

The present invention comprises a new and distinct variety of *Anthurium*, botanically known as *Anthurium andreanum* L., and hereinafter referred to by the variety name 'ANTHDUDKA'. This new *Anthurium* plant is a product of a planned breeding program conducted by the inventor in Bleiswijk, The Netherlands. The objective of this breeding program was to create a new plant with bright red spathes and a compact plant habit intended for small pot sizes (diameter 9 to 12 cm).

The new variety originated from a cross-pollination made in November 2006 in Bleiswijk, The Netherlands. The female parent was a red *Anthurium* pot plant designated 'ANTHOLODOJ' (U.S. Plant Pat. No. 20,254), and the male parent was an orange *Anthurium* plant designated '10520-03' (unpatented).

A single plant was selected in November 2008 and has been asexually reproduced repeatedly by tissue culture in Bleiswijk, The Netherlands over a seven-year period. The present invention has been found to retain its distinctive characteristics through successive asexual propagations.

Plant Breeder's Rights for this variety have been applied for in the European Union on Nov. 6, 2014. 'ANTHDUDKA' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, bright red, cordate spathe;
2) White spadix with yellow tip;
3) Green cordate leaves;
4) The base of the older flowers becomes brown-red; and
5) Hardly no pollen production.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 35-week old plant grown in a greenhouse in Bleiswijk, The Netherlands in January 2016. Colors in the photographs may differ from the color values cited in the detailed botanical description, which accurately describe the actual colors of the new variety.

DESCRIPTION OF THE NEW VARIETY

Figure 1:
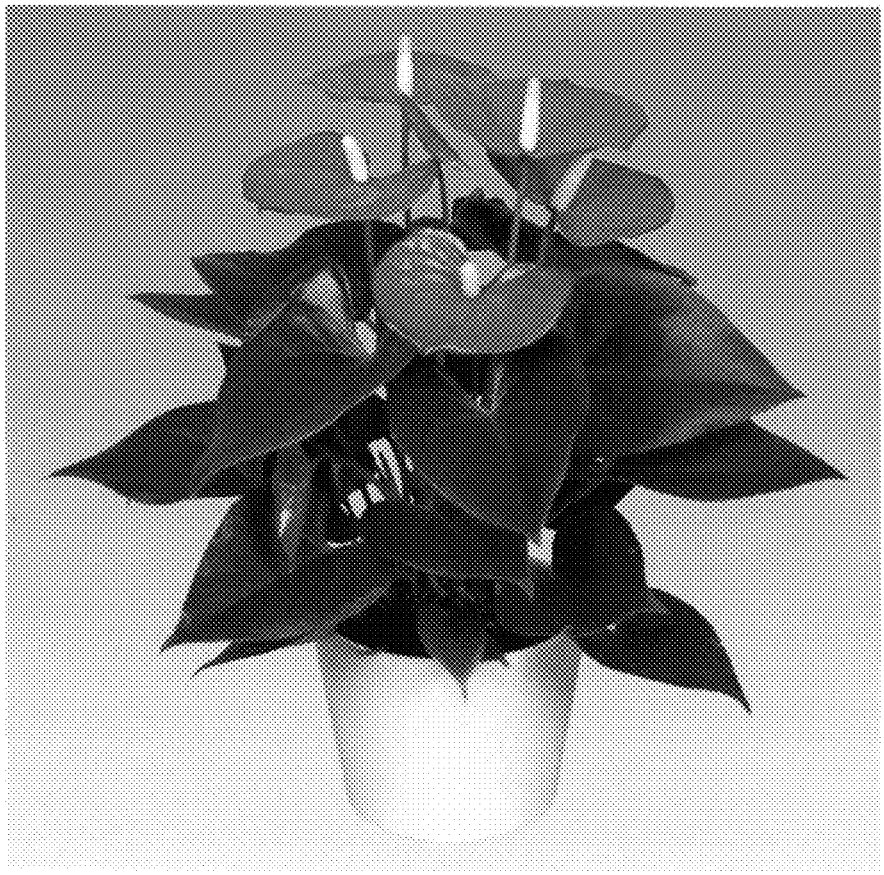
FIG. 1 shows the overall plant habit, including blooms and foliage.
Figure 2:
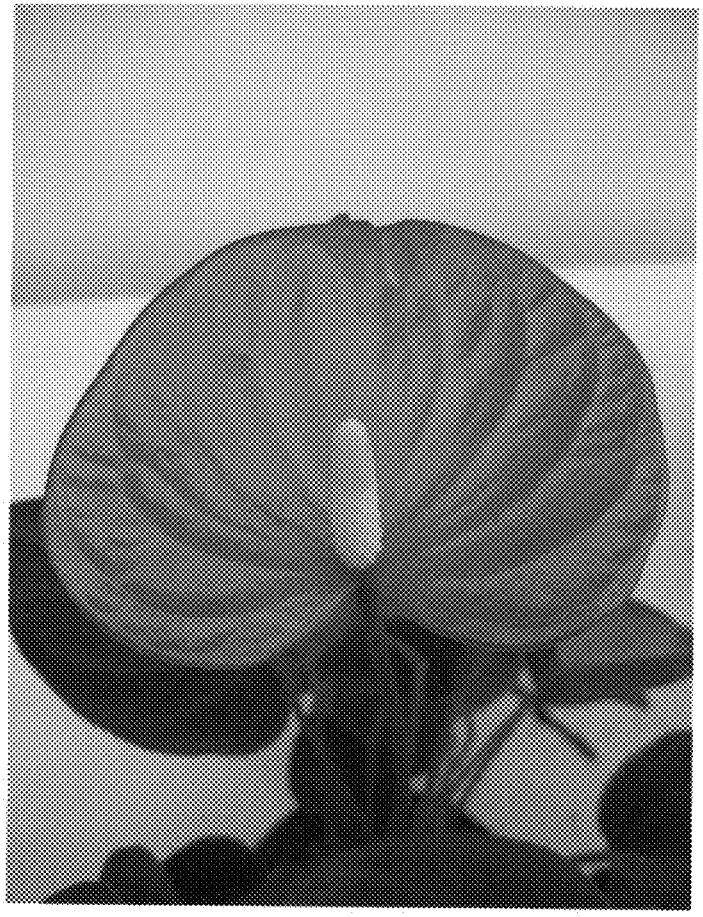
FIG. 2 shows a close-up of the mature spathe.
Figure 3:
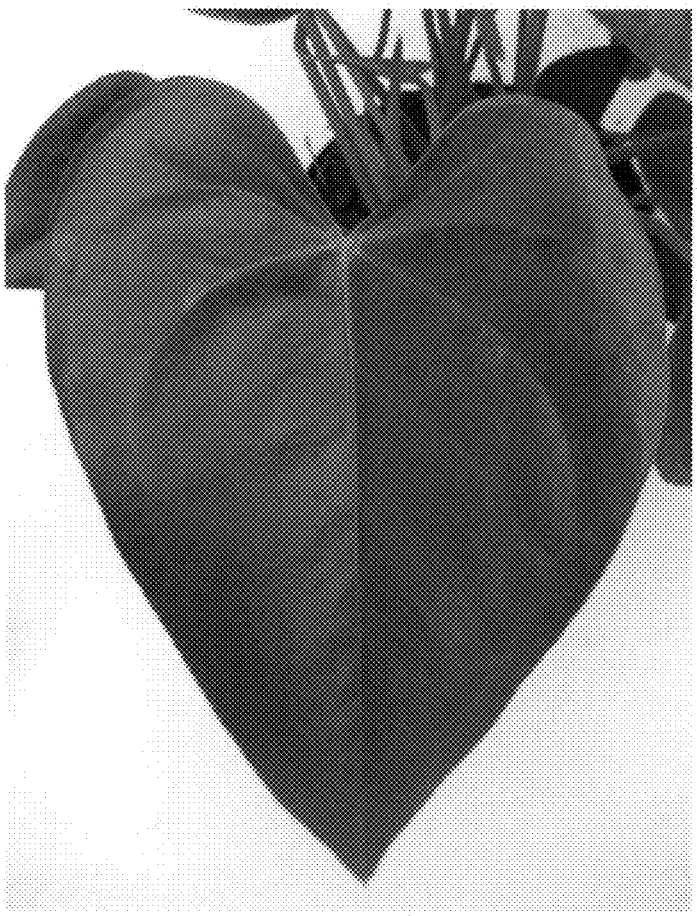
FIG. 3 shows the upper leaf blade surface.

The following detailed description sets forth the distinctive characteristics of 'ANTHDUDKA'. The data which define these characteristics were collected from asexual reproductions carried out in Bleiswijk, The Netherlands. The plant history was taken on 35-week old plants which were planted from tissue culture in 12-centimeter diameter pots and grown in a glass greenhouse between 19° C. and 24° C.

Observations were made in January 2016. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDUDKA'.

Parentage:

*Female parent*.—*Anthurium* plant 'ANTHOLODOJ' (U.S. Plant Pat. No. 20,254).

*Male parent*.—*Anthurium* plant '10520-03' (unpatented).

Plant:

*Propagation*.—Tissue culture.

*Root description*.—Fleshy-creamy white colored roots with small hairy lateral roots having yellow colored root tips.

*Time to produce a finished flowering plant*.—30 to 35 weeks after planting in a 12 cm diameter pot.

*Growth habit*.—Herbaceous perennial.

*Height* (*measured from soil, including inflorescence*).—26.0 cm to 28.0 cm.

*Width* (*measured from leaf tips*).—30.0 cm to 34.0 cm.

Leaves:

*Immature leaves*.—Length: 10.0 cm to 12.0 cm. Width: 6.0 cm to 8.0 cm. Color: Upper surface: RHS 146A. Lower surface: RHS 146B. Texture (both upper and lower surfaces): Shiny.

*Mature leaves*.—Length (fully expanded): 13.0 cm to 15.0 cm. Width: 10.0 cm to 12.0 cm. Shape: Ovate cordate. Apex: Abruptly acuminate. Base: Cordate. Leaf blade angle with the petiole: Between 120 degrees and 130 degrees. Leaf margin: Entire. Color: Upper surface: RHS 147A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Arrangement: Leaf blade has two lobes extending past the petiole. The lobes are non-touching. Length of lobes of mature leaf blades: 2.0 cm to 2.5 cm. Width of lobes of mature leaf blades: 4.5 cm to 5.5 cm. Distance for petiole/leaf junction to highest point on lobes of mature leaf blades: 2.0 cm to 2.5 cm.

*Petiole*.—Cross-section: Round. Diameter: 0.25 cm to 0.3 cm. Length: 8.0 cm to 12.0 cm for a mature leaf size. Color: Mature leaf: RHS 144A. Immature leaf: RHS 144C. Cataphyll color surrounding the petiole: Outside: RHS 180A. Inside: RHS 182C.

*Geniculum*.—Length: 2.5 cm. Width: 0.35 cm to 0.41 cm. Color: RHS 144B.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 95 degrees and 105 degrees; the spathe stands on a wiry peduncle about 7.0 cm to 9.0 cm above the foliage.

*Shape*.—Cordate.

*Apex*.—Acuminate.

*Base*.—Cordate.

*Texture*.—Shiny and blistered.

*Margin*.—Entire.

*Size*.—Length: 7.0 cm to 9.0 cm. Width: 8.5 cm to 9.5 cm.

*Lobes*.—Arrangement: The spathe has two lobes extending past the peduncle. The lobes are non-touching. Length: 1.0 cm to 1.5 cm. Width: 3.5 cm to 4.5 cm.

*Color*.—Just fully open: Upper surface: RHS N45A. Lower surface: RHS 45C. This red color remains for a very long period, more than 30 weeks after opening. Although at the base, the spathe turns to brown-red after some weeks.

Peduncle:

*Shape*.—Erect.

*Cross-section*.—Round.

*Length*.—20.0 cm to 23.0 cm.

*Diameter*.—0.3 cm to 0.4 cm.

*Color*.—RHS N144D.

Flowering time:

*General*.—One small rooted untreated tissue culture plant of 8.0 cm tall will flower, depending on season, after 28 to 32 weeks after planting in a 12 cm pot, and 4 to 6 blossoms will appear. More blossoms appear after some additional weeks so that a full flowering and commercial plant will have 6 to 8 red spathes. Smaller blossoms may occur on less mature plants.

Spadix:

*Size*.—Length: 2.5 cm to 3.5 cm (depending on flower size). Width (at apex): 0.45 cm to 0.5 cm. Width (at base): 0.6 cm to 0.7 cm.

*Shape*.—Columnar.

*Angle from spadix tip to peduncle*.—160 to 170 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 13C. Mature: RHS 155B. Aged: RHS N144A.

Flowers:

*Quantity per spadix*.—200 to 250.

*Spadix flower arrangement*.—Bisexual, rounded in cross-section.

*Shape*.—Rounded.

*Size*.—Length: 0.05 cm to 0.1 cm. Diameter (maximum): 0.1 cm. Color: RHS 156D.

Reproductive organs:

*Stamens*.—Not visible.

*Pollen amount*.—None.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

Disease and pest resistance: None observed.

COMPARISON WITH PARENTAL AND COMMERCIAL VARIETIES

'ANTHDUDKA' differs from the female parent plant 'ANTHOLODOJ' (U.S. Plant Pat. No. 20,254) in that 'ANTHDUDKA' has ovate cordate shaped leaves and spathes, whereas 'ANTHOLODOJ' has elliptical cordate shaped leaves and spathes. Additionally, the spadix length of 'ANTHDUDKA' is shorter than the spadix length of 'ANTHOLODOJ'.

'ANTHDUDKA' differs from male parent plant '10520-03' (unpatented) in that the spathes of 'ANTHDUDKA' are red, whereas the spathes of '10520-03' are orange. Additionally, 'ANTHDUDKA' has ovate cordate shaped leaves, while '10520-03' has elliptical cordate shaped leaves.

'ANTHDUDKA' differs from commercial variety 'ANTHCOZAM' (unpatented) in that 'ANTHDUDKA' has yellow immature spadix, white flowers and red spathes, whereas 'ANTHCOZAM' has orange immature spadix, orange-red flowers and dark red spathes. Additionally, 'ANTHDUDKA' has ovate cordate shaped leaves and flat spathes, whereas 'ANTHCOZAM' has elliptical cordate shaped leaves and wavy spathes.

'ANTHDUDKA' differs from commercial variety 'ANTHEPEDI' (U.S. Plant Pat. No. 18,644) in that 'ANTHDUDKA' has immature spadix that are yellow and spathes that are flat, whereas 'ANTHEPEDI' has immature spadix that are yellow-orange and spathes that are cupped. Additionally, the cataphyll of 'ANTHDUDKA' are grey-red, whereas the cataphyll of 'ANTHEPEDI' are light green.

I claim:

1. A new and distinct variety of *Anthurium* plant named 'ANTHDUDKA', substantially as illustrated and described herein.

* * * * *